(12) United States Patent
Leijon

(10) Patent No.: US 6,706,191 B1
(45) Date of Patent: Mar. 16, 2004

(54) CHROMATOGRAPHIC PROCESS UTILIZING A FLUIDIZED BED

(75) Inventor: Patrik Leijon, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/830,863

(22) PCT Filed: Oct. 31, 1999

(86) PCT No.: PCT/SE99/01965

§ 371 (c)(1),
(2), (4) Date: Aug. 23, 2001

(87) PCT Pub. No.: WO00/25884

PCT Pub. Date: May 11, 2000

(30) Foreign Application Priority Data

Oct. 31, 1998 (SE) .............................................. 9803737
Nov. 8, 1998 (SE) .............................................. 9803813

(51) Int. Cl.⁷ .............................................. B01D 15/08
(52) U.S. Cl. .................. 210/656; 210/198.2; 530/413; 530/417
(58) Field of Search ................ 210/635, 656, 210/659, 198.2; 530/413, 417

(56) References Cited

U.S. PATENT DOCUMENTS

| | | | | |
|---|---|---|---|---|
| 4,976,865 A | | 12/1990 | Sanchez et al. ............. | 210/635 |
| 5,466,377 A | * | 11/1995 | Grandics .................... | 210/635 |
| 5,759,793 A | * | 6/1998 | Schwartz .................... | 210/660 |
| 6,027,650 A | * | 2/2000 | Van Reis .................... | 210/656 |

FOREIGN PATENT DOCUMENTS

| | | | |
|---|---|---|---|
| WO | WO 9520427 A1 | 8/1995 | ................. 210/656 |
| WO | WO 9833572 A1 | 8/1998 | ................. 210/656 |

OTHER PUBLICATIONS

Chang, Y.K., et al., "Ion Exchange Purification of G6PDH from Unclarified Yeast Cell Homogenates Using Expanded Bed Adsorption" Biotechnology and Bioengineering, vol. 49, 1996, pp. 204–216.

* cited by examiner

Primary Examiner—Ernest G. Therkorn
(74) Attorney, Agent, or Firm—Royal N. Ronning, Jr.; Stephen G. Ryan; Yonggang Ji

(57) ABSTRACT

A liquid chromatographic process performed at least partly in a fluidised bed contained in a vessel and comprising particle fluidised by an upwardly directed liquid flow, said process comprising (a) a capture step in which one or more compounds of a sample are captured by the particles and (b) a wash and/or releasing step in which the particles is in form of a fluidised bed through which a liquid flow is passing. The characteristic feature is that the liquid (liquid 1) used in the wash or the releasing step (step 1) is immediately followed by a liquid (liquid 2, step 2) having a higher density than liquid 1 while maintaining the bed in a fluidised state. A liquid chromatographic process having an actual sequence of steps comprising (c) at least a capture step in which a sample deriving from an animal is bound to the particles and (d) two consecutive steps (step 1 and step 2) in which the bed is fluidised by a liquid flow passing through said vessel. The characteristic feature of the process is that the liquid used in step 2 (liquid 2) has a density that is higher than the density of the liquid used in step 1 (liquid 1).

18 Claims, No Drawings

CHROMATOGRAPHIC PROCESS UTILIZING A FLUIDIZED BED

REFERENCE TO RELATED APPLICATIONS

This application is a 371 of PCT/SE99/01965 filed Oct. 31, 1999.

TECHNICAL FIELD

The present invention concerns a new process for performing liquid chromatography in which there is a sequence of steps of which at least two consecutive steps (step 1 and step 2) are in fluidised bed mode by the use of an upward flow.

With respect to various modes of the invention reference is made to copending International Patent Application derived from SE 9803813-6 and SE 9803737-7. This International Patent Application is hereby incorporated by reference.

BACK GROUND TECHNOLOGY

Liquid chromatographic processes are carried out on particle matrices in form of packed or fluidised beds. The processes typically contain at least one step according to type (b) below and one or more functional steps selected from the remaining types of steps (a,c,d,e,f):

a) equilibrating the particles with a liquid conditioning the particles for capture/binding;
b) capturing one or more compounds present in a liquid sample by the particles;
c) washing the particles to which said one or more compounds have become bound;
d) releasing at least one of said one or more compounds from the particles;
e) cleaning the particles; and
f) regenerating the particles.

The capture step (type b) together with the selected steps define an actual sequence in a particular chromatographic process. In an actual sequence there may also be steps other than those outlined above (a–f). A typical sequence comprise the sequence a,b,c,d,e,f(a),b,c,d,e,f(a) . . . possibly with extra steps inserted in the sequence given. f(a) means that step a and step f may coincide and that chromatographic processes can be cyclic.

In each step the particles are treated with an appropriate liquid (solution/buffer) that is aqueous or non-aqueous.

The term "capture" includes that the compound becomes bound to the particles. The binding may occur via the formation of affinity bonds, covalent bonds, entrapment within the particles etc. Examples of affinity are bioaffinity, ionic interaction, hydrophobic interaction etc. The captured compound may be a compound that is to be purified or a contaminant that one wants to separate from another compound or remove from the liquid used in the capture step.

The liquid used in the releasing step typically contains an agent that will release the captured compound, for instance a buffer giving an appropriate pH, a salt giving an appropriate ionic strength, a substance that competitively will inhibit the binding between the captured compound and an affinity ligand/structure on the particles, etc. The term "release" includes release through breaking of affinity bonds, covalent bonds etc. Covalent bonds can be broken by chemical reactions or enzymatically.

The liquid used in a step can change continuously or step wise during a step. Releasing by the aid of a gradient, for instance, is typical for elution on packed beds but has been rare on fluidised beds (Shiloach et al., Sep. Sci. Techn. 34(1) (1999) 29–40). Another example is changing a washing solution during a washing step.

In packed beds, the releasing step typically can consist of one or more substeps. For instance the capture step may mean capture of two or more compounds that bind differently to the particles. For release, the compounds may require different conditions and different compositions of the liquid.

Steps can wholly or partly coincide. The regeneration step, for instance, is primarily related to regeneration of the particles to be used in a second cycle of the process and then coincides with the equilibration step of the second run. The capture step can mean that the compound is only retarded suggesting that the releasing step is at the same time ongoing. In case a contaminant is captured by the particles, possibly in combination with passing through the compound to be purified, release can take place in the cleaning step.

Cleaning steps are often called cip (=cleaning in place). Cip-steps normally comprise high concentration of solutes, such as NaOH, in the liquid used. This means that the liquid for cleaning often has the highest density in an actual sequence.

Each step can be run in a fluidised or packed bed mode with vertical flow that either may be upward or downward. The flow direction may switch between different steps. Plug flow has often been of advantage in chromatography, in particular in capture steps.

The same or different vessels can be used for the various steps of an actual sequence.

During the various steps the particles are placed in a vessel as known in the field. Se WO 9520427 (Amersham Pharmacia Biotech AB), WO 9218237 (Amersham Pharmacia Biotech AB), our copending International Patent Application derived from SE 9803813-6 and SE 9803737-7 etc. Suitable vessels have an inlet end and an outlet end. The vessel is typically placed vertically with the outlet pointing vertically upwards on the top side and the inlet pointing vertically downwards on the bottom side. It can also be the other way round. The inlet and outlet function, respectively, may comprise one or more openings into the vessel interior.

BACK GROUND PUBLICATIONS

Density differences between liquids used in consecutive steps have been used previously in model experiments of fluidised bed purification. These experiments have included various concentrations of glycerol in the washing solution for small scale fluidised bed treatments. The purpose has been to increase the viscosity, and possibly also the density, of the washing solution compared to the solution applied for the adsorption/capture step. See Draeger & Chase, Biosepa-ration 2 (1991) 67-80; Chase et al, Sep. Sci. Techn. 27 (1992) 2021–2039; Chase et al, J. Chromatog. 597 (1992) 129–145; Chase et al, 6th European Congress of Biotechnology (ECB 6), Florence, Italy, Jun. 13–17, 1993; Chase, TIBTECH 12 (1994) 296–303; Chang et al, Biotechn. Bioengin. 48 (1995) 355–366; and Chang et al, Biotechn. Bioengin. 49 (1996) 204–216). The articles discuss that there are certain disadvantages on the subsequent elution (releasing) step due to the viscosity created by the added glycerol and that these disadvantages can be avoided by running the subsequent releasing step in a packed bed mode.

In fluidised bed chromatography liquids of increased densities have often been used when going from an equilibration step to a capture step (the samples are often is relatively dense).

Recently gradient elution has been applied in fluidised bed chromatography. See Shiloach et al., Sep. Sci. Techn. 34(1) (1999) 29–40.

DRAWBACKS OF PREVIOUS TECHNIQUES

In the releasing step of an actual sequence defined above the liquid used contains an agent that will release a captured compound from the particles. This means that the density of a liquid will tend to increase during the releasing step. In case the bed is fluidised by an upward flow there will be a tendency that liquid containing the released compound will be transported downwards simultaneously with the front of the release liquid progressing upwards. The result will be a dilution of the released compound and many times an unfavourable increase in the volume of liquid to be handled in the subsequent processing of the released compound.

Washing liquids may be relatively light. If a washing liquid has a density lower than the density of the liquid of a preceding step it will cause turbulence and lowered efficiency of the washing step. This is particularly pronounced for washing steps that are consecutive to a-capture step because the liquid used in a capture step many times is relatively dense.

These drawbacks will be more pronounced in vessels that do not have a movable outlet adapter compared to vessels that have this type of adapter.

THE INVENTION

The invention is a method for processing a liquid sample containing one or more compounds to be removed by capturing at to least one of them by particles that are brought into contact with the sample. The method comprises an actual sequence as defined above comprising a part sequence of at least two consecutive steps (step 1 and step 2) in which the particles are fluidised. Step 1 precedes step 2.

It has now been fully appreciated that the above-mentioned drawbacks of this kind of part sequences can be minimised if the density of the liquid used in a fluidised bed step is lower than the density of the liquid used in the consecutive fluidised bed step.

The characterizing feature of the method is that the density of the liquid (liquid 2) used in step 2 is higher than the density of the liquid (liquid 1) used in step 1. The bed is kept in a fluidised state during the two steps. The fact that liquids of increasing densities are used for two consecutive steps means that the steps are carried out in the same vessel with liquid 2 replacing liquid 1.

By the expression "the bed is kept in a fluidised state during the two steps" πis meant that plug flow should essentially be maintained during step 1 and 2. This means that the plate number should be $\geq 5$, preferably $\geq 10$ or $\geq 20$ during substantially the whole period of time defined by the two steps. The plate number can be measured as described in the experimental part of WO 9717132.

The density of a liquid used in a step is the density of the liquid as applied to the fluidised bed, i.e. not including the density change that may occur during a step.

In addition to step 1 and step 2, one or more additional steps may be present in the actual sequence used. These extra steps may be selected among equilibration steps, capture steps, washing steps, releasing steps, cleaning steps and regeneration steps and any other step that may be available. One or more up to all such extra steps may be in fluidised mode that preferably is carried out in the same vessel as the part sequence comprising steps 1 and 2. Steps that are not carried out in fluidised mode are supposed to be carried out in packed bed mode. Typical steps that are carried out in packed bed mode are releasing steps and regeneration steps and equilibration steps and combined regeneration/equilibration steps. Packed bed mode steps can be performed either with upward or downward flow as is commonly known for this kind of beds. Step 1 may be consecutive to a fluidised bed step or to a sequence of consecutive fluidised bed steps that together with steps 1 and 2 form a sequence that utilizes liquids of increasing densities. Similarly step 2 may have an immediate subsequent fluidised bed step or an immediate subsequent sequence of fluidised bed steps that together with steps 1 and 2 forms a sequence that utilizes liquids of increasing densities.

The inventive concept is preferably applicable when at least one of step 1 and step 2 is a functional step, for instance selected among a–f above. Examples of part sequences in which both step 1 and step 2 are functional steps are:

| Alternative | Step 1 | Step 2 |
|---|---|---|
| I | Washing step | Releasing step |
| II | Releasing step | Cleaning step |
| III | Releasing step with a first releasing agent | Releasing step with a second releasing agent |
| IV | Capture step | Washing step |
| V | Washing step with a first washing liquid | Washing step With a second washing liquid |
| VI | Density decreasing step | Any functional step a–f |
| VII | Cleaning step | Regeneration step or equilibration step |
| VIII | Equilibration step | Capture step |

The table assumes that the liquids have been selected so that step 2 has an increased density compared to step 1.

Density decreasing step: The feature of having fluidised bed steps in which a denser liquid is coming before a lighter liquid may have advantages when dealing with dense and viscous liquids, for instance capture liquids. In these cases it may be difficult to increase the density further. This will be overcome by having a zone of lighter liquid (liquid 1, step 1), for instance a "wash solution", to pass the bed, and then in the next step (step 2) increase the density of the liquid (liquid 2). The drawback is that the risk for bed turbulence will increase but the liquid exiting the bed will anyhow be lighter than the dense liquid used prior to liquid 1. Liquid 2 can be, for instance a true washing liquid, with an increased density relative the "wash" solution. With respect to the step that precedes step 1, this principle may be applicable to any of steps a–f but in particular to step 1 being a capture step.

The increase in density when going from step 1 to step 2 includes adding density-increasing agents to the liquid used in step 1 ("wash" solution). These agents should not decrease the binding of the compound to the particles. Typical agents are uncharged soluble compounds such as uncharged compounds having carbohydrate structure. See below.

Step 2 may be used to keep the liquid used in the preceding step (step 1) and consecutive step (step 3) physically apart in the vessel used. In this variant steps 1 and 3 may be selected from steps a–f above. By applying the principles of the invention, the liquid used in step 2 will have a density intermediate to the densities of step 1 and step 3. This variant of the invention is particularly useful when step 1 is a releasing step. During a releasing step the density of the liquid used will increase which in turn will cause a dilution of the sample and an increased volume. It may therefore be advantageous to elute with a denser liquid immediately after the releasing step, i.e. before the cleaning step or before a second compound is released, possibly by another releasing agent and/or by a liquid having a higher density containing the same releasing agent. The liquid used in step 2 of this variant may be-the same as the liquid used in step 1 but with a densifying substance added. This substance may be the same as or different from the releasing agent in liquid 1. Other alternatives for densifying agent are glycerol, other carbohydrates, salts etc.

A packed bed mode step may be inserted in the actual sequence used if there is a need to bring down the density of the liquid of a subsequent step. For instance after a certain step, it may not be feasible or practical to increase the density further. This use of packed mode bed steps provides a simple and practical way of making a process according to the invention cyclic. The liquid used in this kind of packed bed mode steps is preferably less dense than the two liquids used in the closest surrounding steps. Once the density of the liquid for a step has been reduced then liquids of increasing densities can be used in consecutive steps. In principle any step a–f above can be carried out in packed bed mode as described in this paragraph. For typical packed bed mode steps see above.

An alternative way for enabling cyclic processes is to use part sequence VI in the table above provided that the liquid in step 1 has a sufficiently low density. This in practice means that a turbulent bed has to be accepted in this step.

Great advantages will be accomplished in case step 1 is a washing or a releasing step.

An increase in density can be achieved by increasing the concentration of a substance that is soluble in the liquid used and has a density-increasing effect on the liquid. For aqueous liquids, typical examples of substances are salts such as halides (typically chlorides), phosphates, sulphates etc, for instance soluble metal and ammonium salts thereof, and uncharged substances such as soluble carbohydrates, for instance glycerol and other mono- or oligosaccharides. With respect to organic compounds they should as a rule have a density higher than the liquid in order to provide an increased density when added to the liquid. Typically they should have a relatively large molecular weight, for instance reflected in number of carbon atoms being $\geq 3$, such as in carbohydrates with $\geq 4$ carbon atoms.

It is important to select the density-increasing agent so that it will not interfere in an undesired way with the binding between the compound and the particle in the step involved. In steps preceding a releasing step the agent should not be able to act as a releasing agent for the release intended in the step or in any other subsequent releasing steps In releasing steps the agent should not be able to counteract the release intended.

The required relative difference in density between two consecutive fluidised bed steps will depend on various factors, for instance desired number of theoretical plates. This number in turn will depend on the column design including the distributor design. Our results so far achieved suggest that the relative increase in density can be as low as 1/10000 between two consecutive fluidised bed steps in case the system is optimised to a plug flow corresponding to >35 theoretical plates in the fluidised/expanded bed. Thus the relative increment in density for each consecutive fluidised bed step can be $\geq 1/10000$, such as $\geq 1/1000$ or $\geq 1/100$ or $\geq 1/10$ of the density of the liquid used in the immediately preceding fluidised bed step (for instance selected from steps a–f as defined above). Depending on the system used, the number of theoretical plates can be down to 5 provided that the relative density difference for the liquids is sufficiently high between two consecutive fluidised bed step. Thus systems providing, for instance, $\geq 5$ such as $\geq 15$ and $\geq 35$ theoretical plates in the fluidised bed may be used.

An increase in density is often accompanied by an increase in viscosity. Some substances have a more pronounced ability to increase the viscosity than others. This may have unfavourable effects in fluidised bed systems. It may therefore be beneficial to switch from a pronounced to a less pronounced viscosity increasing substance when increasing the density of the fluidising liquid between two fluidised bed steps.

In absolute figures the density of the liquid used should be above the pure liquid without any density-increasing agent added. The upper limit is determined by the density of the particles and/or by practical considerations, such as costs for density-increasing materials. For aqueous liquids this means that the density of the liquids for consecutive fluidised bed steps may change within the interval 0.98 to 1.20 or to 1.50 g/cm$^3$, with preference for 1.00 to 1.15 g/cm$^3$. The lower limit 0.98 g/cm$^3$ accounts for the fact that density-decreasing agents may be added, such as water-miscible organic solvents, for instance methanol, ethanol etc. By the use of heavier particles, for instance with densities $\geq 1.20$ g/cm$^3$, the upper limit of the density interval can potentially be extended upwards and more dense liquids could accordingly be used. This means that aqueous liquids used in two consecutive fluidised bed steps according to the invention may have a difference in density in the range starting just above 0 and going up to at least 0.52 g/cm$^3$ with preference for at least 0.22 g/cm3. Analogous ranges can be set up in case one selects to use non-aqueous liquids.

The density of the particles should be $\geq 1.05$ g/cm$^3$, preferably $\geq 1.14$ g/cm$^3$, and even $\geq 1.20$ g/cm$^3$ such as $\geq 1.30$ g/cm$^3$. An upper limit of 5–6 g/cm$^3$ can be envisaged. Suitable particles are described in WO 9218237 (Amersham Pharmacia Biotech AB); WO 9717132 (Amersham Pharmacia Biotech AB); WO 9833572 (Amersham Pharmacia Biotech AB); and WO 9200799 (Kem-En-Tek/Upfront Chromatography A/S). Suitable particles often contain inorganic material as a densifying material. Suitable particles may also contain synthetic polymers. Polymers can be divided into purely synthetic polymers, semisynthetic polymers and biopolymers. Synthetic polymers may have monomeric units selected amongst acryl amides, methacrylamides, hydroxy alkyl acrylates, hydroxy alkyl methacrylates, styrenes, divinyl benzenes etc. Semisynthetic polymers comprise for instance cross-linked biopolymers and copolymerisates thereof and grafted polymers exhibiting structures originating from biopolymers. Biopolymers comprise polysaccharides, such as dextran, agarose, cellulose, starch and pullulan. Well known particles that have been used for fluidised bed applications are sold under the trade mark Streamline (Amersham Pharmacia Biotech AB, Uppsala, Sweden) and belong to a group of particles comprising both density increasing material, often inorganic, and hydrophilic organic material, typically polymeric.

The process temperature for various steps involved depends on the liquid used and the compound to be captured, among others. For aqueous solutions the process temperature may be VIII Equilibration step Capture step from 0° C. up to e.g. 70–90° C. although for practical considerations the temperature is often in the interval 0–50° C. For other liquids other ranges apply.

The inventive method has its largest use in processes of relatively large productivity. This means that the flow velocities used should be at least 70–3000 cm/h, preferably from 80–90 cm/h and upwards. The vessels should have a cross sectional area that typically corresponds to the area of a square having a side of at least 10 cm, such as at least 15 cm. The cross-sectional area referred to is perpendicular to the liquid flow fluidising the particles.

As discussed above, the actual sequence may comprise one or more steps that are best performed in packed bed mode, possibly by reversing the flow relative the particles. By starting from a step in fluidised mode in a traditional vessel, this may be accomplished by allowing the particles to sediment to a "packed bed" and then apply an upward or downward flow through the vessel. An alternative utilizes a tiltable vessel that is tilted 180° when changing bed mode. See FIGS. 7a–b of our copending International Patent Application deriving from SE 9803813-6 and SE. This type of change in flow direction may be particularly valuable in case the particles are to be regenerated, for instance to be used in a second run of the same process. The advantages derives from the fact that the cleaning step often makes use of the liquid with the highest density while a combined regeneration/equilibration step utilizes a liquid of low is density. An alternative to a packed bed mode step, for instance via tilting, may be to accept a lowered plate number during the releasing step and perform the step under fluidising conditions with a liquid having a lowered density compared to the preceding step. See above.

Packed bed steps may be combined with fluidised bed steps in devices designed therefore. See copending International Patent Application with priority from SE 9803813-6 and SE 9803737-7. Hence, the full actual sequence of the inventive process may be carried out in one common vessel device in which the collector arrangement is maintained at a fixed distance from the distributor arrangement during consecutive fluidised bed steps. The preferred type of vessels thus may have fixedly mounted collector and distributor arrangements. This does not exclude that the full sequence also can be performed in a vessel having a movable outlet adapter, for instance as described in WO 9520427 (Amersham Pharmacia Biotech AB) and WO 9218237 (Amersham Pharmacia Biotech AB). Neither does it exclude a system of vessels in which different vessels are dedicated to fluidised bed steps and packed bed steps, respectively (see FIGS. 8–10 in copending International Patent Application deriving from SE 9803818–6 and SE 9803737-7).

The above-mentioned density ranges for liquids refer to densities measured at the actual process temperature. For particles the densities refer to particles in the wet state having been soaked with the pure liquid used, for instance water. Plate numbers refer to those having been obtained by the method described in WO 9717132.

Applications in Which the Invention can be Used

The invention is primarily used in liquid chromatography techniques. Examples are size exclusion (gel permeation) chromatography and adsorption techniques and techniques involving formation of covalent bonds between the particles and the compound to be removed from the liquid. Adsorption techniques are also called affinity chromatography. The important variants are ion exchange chromatography and techniques based on other affinity principles, such as bioaffinity, hydrophobic interaction (HIC), chelating interaction etc. The structure on the particles causing adsorption is often called affinity ligand or affinity structure.

The compound to be captured on the particles may be ions, for instance metal ions, and inorganic and organic compounds, for instance biomolecules, such as proteins, carbohydrates, lipids, amino acids, hormones etc. In case of proteins they may have been produced recombinantly in host cells (bacteria, yeast, mammalian, plant and insect cells, for instance), by in vitro translation or in transgenic animals, such as transgenic mammals and transgenic avians, for instance budgerigars. In particular production of human proteins in cows, sheeps, goats, horses etc may be mentioned. Important proteins are native and recombinant forms of plasma proteins, such as blood coagulation factors, immunoglobulins, ATIII, $\alpha$1-antitrypsin, serum albumin etc; whey proteins such as lactoferrin and lactoperoxidase; enzymes; peptide or protein hormones such as growth hormones, insulin etc; erythropoetin; protein antigens and their fragments to be used, for instance, as vaccines or agents in hyposensitization therapy; and other proteins that are of therapeutic interest. Among blood coagulation factors FVIII, FVII, FIX etc may be mentioned. Among immunoglobulins various forms of monoclonal antibodies (IgA, IgD, IgE, IgG, IgM) including fragments and fused forms thereof may be mentioned. Industrial enzymes such as those used in washing powders and in other compositions intended for cleaning are of potential importance.

The samples to be applied to the fluidised bed are liquids containing the compound to be bound to the particles in the capture step. This includes fermentation broths, and other biological fluids derived from animals, such as mammals and other vertebrates, and evertebrates. In particular it includes transgenic animals as discussed above. Particular biological fluids from animals are blood, serum, urine, milk (including whey) etc and other samples containing the biomolecules discussed above together with sticky and/or particulate components.

The original sample may have undergone a number of pretreatment steps before being applied in a capture step. Pretreatment steps may be dilution, concentration, desalting, removal of specific components, centrifugation, filtration, dialysis, ultrafiltration, pH-adjustments etc. A typical procedure is to dilute the sample in a buffer providing the same conditions as the buffer used in the equilibration step. An alternative is to equilibrate the particles to the conditions provided by the sample. These procedures are typically carried out after the appropriate pretreatments of an original sample.

The invention will find uses within a large variety of technical fields, such as food industry, water purification and water deionisation, drug manufacturing, metal refining etc, A particular important aspect of using density differences as described herein is for working up a compound from a sample deriving from a biological fluid of an animal, in particular a transgenic animal. In this aspect the process as such comprises an actual sequence of steps with characteristic features as defined above. The biological fluids concerned and their origin have been discussed above. The biological fluid concerned are primarily those that contains particulate and/or sticky components and/or are more or less highly viscous, for instance blood, serum, plasma, milk, whey etc. The compounds are the same as discussed above.

The preferred modes of the invention utilize vessels and systems as described in copending International Patent Application derived from SE 9803813-6 and SE 9803737-7.

The invention will now be illustrated in the experimental part. The invention is further defined by the appended claims.

EXPERIMENTAL PART

Test of Using Density Differences in Preventing Mixing Between Subsequently Incoming Liquids in a Liquid Fluidised Bed The background of this test is to be able to run the column in expanded mode throughout all the operating steps without loosing performance due to instability of the bed (mixing, channeling etc.). The theory was that the density of the liquids is the key factor whether two different liquids will mix or not in a fluidised bed and not the viscosity of the liquids. This means that a heavy liquid that is pumped into an expanded bed column (even distribution of liquid) which contains a lighter liquid, will create a sharp boundary between the two liquids and no mixing will occur. Whilst on the other hand, a light liquid pumped into a heavy liquid will cause severe mixing. By using increasing densities from liquid to liquid no mixing will occur and thereby a minimum of buffer consumption will be gained.

Experiment

A conventional column (200 mm in diameter and 1000 mm in height) with the existing distributor design was used (perforated plate with a mesh; Streamline, Amersham Pharmacia Biotech AB, Uppsala, Sweden). Streamline DEAE gel was used in this experiment. Five different liquids were pumped (at 300 cm/h) into the column from bottom to top in the following order:

| Liquid | Density | Comments |
|---|---|---|
| 50 mM NaCl | 1.000 | The bed was equilibr. ½ hr |
| 5% (dry weight) yeast susp. | 1.017 | More viscous than 50 mM NaCl |
| 10.6% glycerol solution | 1.022 | More viscous than the yeast susp. |
| 0.82M NaCl | 1.030 | Less viscous than the glycerol sol. |
| 1M NaOH | 1.040 | More viscous than 0.82M NaCl |

The result was sharp boundaries between the different liquids in the presence of a fluidised bed and thereby no mixing of the liquids.

This experiment proved that the liquid density is the governing factor when it comes to stable non-mixing behaviour between different liquids even in the presence of a fluidised bed.

What is claimed is:

1. A liquid chromatographic process performed at least partly in a fluidised bed contained in a vessel and comprising particles fluidised by an upwardly directed liquid flow, said process comprising
   (a) capturing one or more compounds of a sample by the particles; and
   (b) washing and/or releasing the particles in a fluidised bed through which a liquid flow is passing,
wherein a liquid (liquid 1) used in the wash or the releasing step (step 1) is immediately followed by adding a second liquid (liquid 2, step 2) having a higher density than liquid 1 while maintaining the bed in a fluidised state.

2. The process of claim 1, wherein the liquid 2
   (a) does not have any significant release effect or final cleaning effect; and
   (b) is used for separating the liquid 1 containing the released compound from a liquid 3 (step 3) that is added subsequent to liquid 2, and for instance is used for cleaning.

3. The process of claim 2, wherein liquid 1 and liquid 2 have a density difference caused by a difference in concentration of a soluble substance.

4. The process of claim 2, wherein the liquid 1 contains a releasing agent and is used for release of a compound captured on the particles and the liquid 2 has an increased density compared to liquid 1 due to the presence of a substance other than the releasing agent.

5. The process of claim 1, wherein the vessel has a cross sectional area corresponding to the area of a square having a side of at least 10 cm.

6. The process of claim 1, wherein
   (a) the vessel has an inlet end and an outlet end; and
   (b) the distance between the inlet end and the outlet end are kept essentially constant during at least two consecutive fluidised bed steps.

7. The process of claim 1, wherein either (a) the distributor and collector arrangements of the vessel are fixedly mounted, or (b) the outlet end is movable relative the inlet end.

8. A liquid chromatographic process performed at least partially in a fluidised bed contained in a vessel having an actual sequence of steps comprising
   (a) capturing a sample, derived from an animal, on the particles; and
   (b) two consecutive steps (step 1 and step 2) in which the bed is fluidised by an upward liquid flow of two different liquids (liquid 1 and liquid 2) passing through said vessel,
wherein the liquid 2 has a density that is higher than the density of the liquid 1.

9. The process of claim 8, wherein step 1 is a releasing step and step 2 is a cleaning step.

10. The process according to claim 8, wherein step 1 is a washing step and step 2 is a releasing step.

11. The process according to claim 8, wherein step 1 is an equilibration step and step 2 a capture step.

12. The process according to claim 8, wherein step 1 is a density-decreasing step which is preceded by an additional step utilizing a liquid having a higher density than used in step 1.

13. The process according to claim 12, wherein step 2 is a washing step.

14. The process according to claim 8, further comprising a releasing step which is performed in packed bed mode.

15. The process according to claim 8, wherein the capture step is in fluidised bed mode.

16. The process according to claim 8, wherein the process is cyclic with each cycle ending with a regeneration step that is the equilibration step for a subsequent cycle.

17. The process according to claim 15, wherein the release step, or the cleaning step or the regeneration/equilibration step is performed in packed bed mode.

18. A liquid chromatographic process carried out in a vessel and having an actual sequence of steps comprising
   (a) at least a capture step in which a sample containing one or more compounds which are derived from cultured mammalian cells are bound to the particles and
   (b) two consecutive steps (step 1 and step 2) in which the bed is fluidised by an upward liquid flow passing through said vessel,
wherein a liquid used in step 2 (liquid 2) has a density that is higher than the density of a liquid used in step 1 (liquid 1).

* * * * *